US006649174B2

(12) United States Patent
Najdek et al.

(10) Patent No.: US 6,649,174 B2
(45) Date of Patent: Nov. 18, 2003

(54) DUAL PHASE COSMETIC COMPOSITION

(75) Inventors: Linda Najdek, E. Islip, NY (US);
Derron T. Peck, Manorville, NY (US);
Elena M. Ciriello, Yonkers, NY (US);
Ralph Vitale, Centereach, NY (US)

(73) Assignee: E-L Management Corp., New York, NY (US)

( * ) Notice: Subject to any disclaimer, the term of this patent is extended or adjusted under 35 U.S.C. 154(b) by 0 days.

(21) Appl. No.: 09/074,051

(22) Filed: May 7, 1998

(65) Prior Publication Data

US 2002/0098209 A1 Jul. 25, 2002

(51) Int. Cl.[7] .................. A61K 9/107; A61K 47/32
(52) U.S. Cl. ................ 424/401; 514/772.5; 514/844; 514/938; 510/138; 510/159; 516/148
(58) Field of Search ................. 424/401, 400; 514/844–846, 772.5, 772.6, 938; 510/138, 159; 516/148

(56) References Cited

U.S. PATENT DOCUMENTS

| 4,335,103 A | | 6/1982 | Barker et al. |
| 4,438,095 A | | 3/1984 | Grollier et al. |
| 4,980,155 A | | 12/1990 | Shah et al. |
| 5,138,043 A | | 8/1992 | Polovsky et al. |
| 5,165,917 A | | 11/1992 | Zabotto et al. |
| 5,384,334 A | | 1/1995 | Polovsky et al. |
| 5,405,878 A | | 4/1995 | Ellis et al. |
| 5,468,496 A | | 11/1995 | Touzan et al. |
| 5,658,559 A | * | 8/1997 | Smith |
| 5,698,211 A | * | 12/1997 | Narayanan |
| 5,871,758 A | * | 2/1999 | Nagy et al. |
| 5,993,830 A | * | 11/1999 | Freij |

FOREIGN PATENT DOCUMENTS

| EP | 0 490 750 | 6/1992 |
| JP | 09255523 | 9/1997 |
| WO | WO 92/09266 | 6/1992 |
| WO | WO 98/31339 | 7/1998 |

* cited by examiner

Primary Examiner—Edward J. Webman
(74) Attorney, Agent, or Firm—Dorene M. Price, Esq.; Karen A. Lowney, Esq.

(57) ABSTRACT

The present invention relates to a liquid dual phase cosmetic or pharmaceutical composition comprising an oil phase and an aqueous phase, the composition containing as a demixing agent a film forming agent such as polyvinylpyrrolidone and derivatives thereof. The compositions of the invention are particularly useful as makeup removers.

13 Claims, No Drawings

DUAL PHASE COSMETIC COMPOSITION

FIELD OF THE INVENTION

The present invention relates to cosmetic compositions. In particular, the invention relates to two-phase cleansing compositions which are particularly useful in makeup removal

BACKGROUND OF THE INVENTION

Dual phase skin cosmetic compositions are currently very popular, in that they provide a broad range of cleansing/conditioning potential within a single product, and are also aesthetically appealing to the consumer. Typically, the dual phase product contains an aqueous phase and an oil phase, each adapted to removing a particular type of residue from the skin, or delivering a particular type of active In a common use, for example, the aqueous phase of a dual phase cleansing composition is designed to remove water-soluble material from the skin, while the oil phase is designed to remove oil-based, or "waterproof" material from the skin.

A number of factors must be considered in making a successful dual phase product. For example, in order to function properly, the two phases must be vigorously mixed, providing a temporary apparently homogeneous single phase product which delivers both phases to the region to be treated simultaneously. This typically means that the product must contain one or more surfactants or emulsifiers, which will render the two phases at least temporarily compatible during the mixing and application stage Surfactants are also frequently useful in the removal of waterproof makeup. Unfortunately, many such emulsifiers are drying to the skin and/or are Irritating to users, and in particular cannot be routinely used in the eye area.

On the other hand, however, it is also desirable that the two phases separate quickly after use, as the emulsified product has a cloudy appearance that is unappealing to consumers. After prolonged, continuous mixing of the two phases during regular use, the time it takes for the phases to separate becomes longer and longer, and the product rapidly loses its initially attractive appearance. Moreover, oil soluble actives may be unstable if they remain in prolonged contact with the aqueous phase, and therefore, the amount of time spent in contact with the water phase should be minimized. As can readily be seen, these two aspects of the dual phase product, namely, the need for rapid and complete emulsification followed by rapid and complete separation, are at odds with each other, and to achieve both satisfactorily in a single product, in a way that is both cosmetically acceptable and attractive to the user, is often difficult The present invention, however, provides a dual phase product in which the phases mix well and completely, and yet demixing is accomplished rapidly after use Moreover, the product is non-irritating, and when used as a makeup remover, is highly successful in removing even the most difficult to remove oil-based cosmetics

SUMMARY OF THE INVENTION

The present invention relates to a liquid dual phase cosmetic or dermatological composition comprising an aqueous phase and an oil phase, at least one of the phases containing as a demixing agent, a film forming agent In a preferred embodiment, the demixing agent is a polyvinylpyrrolidone (hereinafter referred to as "PVP") or a copolymer thereof The compositions of the invention are particularly useful when employed as a makeup remover, but may also be used for skin conditioning, or delivery of cosmetic or therapeutic active agents to the skin for the treatment and/or amelioration of various skin conditions.

DETAILED DESCRIPTION OF THE INVENTION

The demixing agents used in the present dual phase compositions are well-known in the art for being useful as film forming agents and for being useful in improving water resistance and wear of compositions However, it has not been previously known that they can be used to facilitate rapid separation of phases in a two phase emulsion. In addition to this function, however, these demixing agents have the additional advantage of being extremely mild, and non-irritating. In particular, they do not appear to cause any irritation when in contact with the eye, which cannot be said of many other demixing agents.

Any film-forming agent may be used in the compositions of the invention. Examples of useful categories of demixing agents include acrylic acid polymers and copolymers, such as cyclo alkyl methacrylate copolymer; chitin or chitosan or derivatives thereof, or polyquaternium film formers, such as polyquaternium-11. A preferred demixing agent is PVP or a copolymer thereof. Particularly preferred are PVP/hexadecene copolymer and/or PVP/polycarbamyl polyglycol ester. PVP/hexadecene copolymer is available commercially under the tradename Ganex V-216 ®, from ISP Sutton Labs of Chatham, N.J. Other demixing agents include for example, PVP/dimethylaminoethylmethacrylate copolymer, PVP/eicosene copolymer, PVP/ethyl methacrylate/methacrylic acid copolymer, PVP/VA copolymer, PVP/1-triacontene, and listings of film formers in the CTFA Cosmetic Ingredient Handbook, incorporated herein by reference.

The demixing agent is added to either the oil phase or the water phase of the composition, usually in an amount of from about 0 001 to about 10 percent, preferably in an amount of about 0.01 to about 1 percent. Dual phase compositions prepared with such a demixing agent emulsify rapidly and uniformly upon vigorous shaking, and demulsify completely upon resting within approximately 5 to 20 minutes. The remainder of the composition is formulated depending on the nature of the desired end product The ratio of the oil phase to aqueous phase is not critical, and can be vaned in accordance with the type of product, but will generally be between 30:70 to 70:30, more preferably between 40.60 to 60.40 Most preferably, the aqueous phase is present as a higher weight percent than the oil phase. The aqueous phase may be any cosmetically acceptable water based material, such as deionized water, or floral water.

The oil phase may be any cosmetically or pharmaceutically acceptable oil, such an oil being defined for the present purpose as any pharmaceutically or cosmetically acceptable material which is substantially insoluble in water. As the oils can perform different functions in the composition, the specific choice is dependent on the purpose for which it is intended. The oils may be volatile or non-volatile, or a mixture of both. For example, suitable volatile oils include, but are not limited to, both cyclic and linear silicones, such as cyclomethicone, octamethylcyclotetrasiloxane, and decamethylcyclopentasiloxane, or straight or branched chain hydrocarbons having from 8–20 carbon atoms, such as decane, dodecane, tridecane, tetradecane, and C8–20 isoparaffins.

Non-volatile oils include, but are not limited to, vegetable oils, such as coconut oil, jojoba oil, corn oil, sunflower oil, palm oil, soybean oil, carboxylic acid esters such as isostearyl neopentanoate, cetyl octanoate, cetyl ricinoleate, octyl palmitate, dioctyl malate, coco-dicaprylate/caprate, decyl isostearate, myristyl myristate, animal oils such as lanolin and lanolin derivatives, tallow, mink oil or cholesterol; glyceryl esters, such as glyceryl stearate, glyceryl dioleate, glyceryl distearate, glyceryl linoleate, glyceryl myn state, non-volatile silicones, such as dimethicone, dimethiconol, dimethicone copolyol, phenyl trimethicone, methicone, simethicone; and non-volatile hydrocarbons, such as isoparaffins, squalane, or petrolatum.

The composition also may contain other cosmetically or therapeutically useful components. It may, for example, be desirable to incorporate other surfactants into the formulation, again depending on the intended purpose of the formulation, for example, as cleansing agents to assist in wetting skin, emulsifying oils or solubilizing soil on skin or as foaming agents. The surfactants employed may be any that are traditionally used for cosmetic or pharmaceutical purposes, and may be selected from nonionic, anionic, cationic or amphoteric surfactants, the identities of which are well known to those skilled in the art. Additional surfactants may be distributed in either or both of the phases of the formulation, and selection is limited only by a given surfactant's compatibility with the phase into which it is incorporated, and by the location to which the composition is to be applied. Other potentially useful components of the formulation include emollients, humectants, fragrances, preservatives, and buffers. Such materials are routinely used in cosmetic products, and listings of appropriate materials can be found, for example in the International Cosmetic Ingredients Handbook, Third Edition, 1996 (CTFA).

As noted above, the formulation can also be used for therapeutic or quasi-therapeutic purposes, and therefore may also comprise useful active ingredients, for the purposes of treating both the skin and hair. Useful active ingredients include, but are not limited to antioxidants, antimicrobials, sunscreens, analgesics, anesthetics, anti-acne agents, anti-dandruff agents, antidermatitis agents, antipruntic agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, antihistamine agents, skin lightening agents, depigmenting agents, wound-healing agents, vitamins, corticosteroids, tanning agents, or hormones. The location of the active in the formulation is determined by its solubility and/or stability in either oil or water.

The formulations of the present invention are useful for a variety of purposes, including skin or hair cleansers, skin or hair treatment products, sunscreen or suntanning products, and the like. In a particularly preferred embodiment, however, the composition is used for removing makeup. As already noted, the demixing agents, because of their mildness, are eminently well-suited to being employed in a product which is usable around the eye. When combined with an appropriate group of additional components, particularly in the oil phase, the resulting makeup remover successfully cleans skin surfaces, particularly eyes and lips, of even the most transfer-resistant of currently used cosmetics, while remaining gentle and non-irritating to the user.

In this preferred embodiment, the oil phase contains a combination of both volatile and non-volatile oils. The volatile oil portion is preferably a volatile hydrocarbon present in amounts of from about 30–70%, and more preferably 40–60%, and the non-volatile present at about 0.1–10%, preferably 0.2–5% by weight of the total composition. In a particularly preferred embodiment, the oil phase contains a blend of oils comprising isododecane at 25–40% by weight of the total composition, a volatile $C_{16}$ isoparaffin at 15–30% by weight of the total composition, and the non-volatile silicone at 0.1–1% by weight of the total composition.

The non-volatile portion of the oil phase is preferably a non-volatile silicone oil. A preferred non-volatile silicone is dimethicone In a particularly preferred embodiment, the amount of volatile oil used is considerably higher than that of the non-volatile oils; for example, the volatile oil will be present in an amount of about 30–70%, preferably about 40–60%, of the total composition, and the non-volatile oil in an amount of about 0.1–10%, preferably about 0.2–5% of the total composition.

In another embodiment, for example, the volatile oil portion contains a combination of a volatile silicone and a volatile hydrocarbon. More specifically, the oil phase contains a blend of oils comprising a low molecular weight cyclic silicone at 25–40% by weight of the total composition, a volatile $C_{16}$ isoparaffin at 15–30% by weight, and the non-volatile silicone at 0.1–1% by weight of the total composition.

In this preferred embodiment, it may be desirable to provide an additional small amount of surfactant in the oil phase to facilitate removal of the cosmetic residue from the skin. The amount of surfactant added is preferably no more than 5%, and more preferably is in the range of 0.1–1%. The surfactant may be of any type, i.e., anionic, nonionic, cationic or amphoteric; however, if the makeup remover is intended for use in the eye area, it is preferred that the surfactant should be a mild surfactant, such as LIPO-PEG-2DL or disodium cocoaamphoidacetate (Miranol).

The invention is further illustrated in the following non-limiting examples

EXAMPLES

1. The following illustrates a formulation of the present invention:

| MATERIAL | % BY WT |
| --- | --- |
| Isododecane | 30 |
| Isohexadecane | 20 |
| Dimethicone | 0.5 |
| PVP/hexadecene copolymer | 0.1 |
| PEG-4 Dilaurate | 0.4 |
| Purified water | 45 |
| Sodium chloride | 1 |
| Potassium phosphate | 0.2 |
| Phenoxyethanol | 0.5 |
| Glycerin | 0.2 |
| Hexylene glycol | 2 |
| Methylparaben | 0.1 |

The components are combined as follows: the oil phase components, isododecane, isohexadecane, silicone and PEG-4 dilaurate are mixed with PVP/hexedecene copolymer (Ganex V-216®), and the water phase components, sodium chloride, potassium phosphate, hexylene glycol, fragrance, preservative and water are mixed together First the oil phase is added to the selected container, then the water phase is added.

What we claim is:

1. A liquid dual phase makeup removal composition comprising an oil phase and an aqueous phase, each phase being separate from the other before and after being mixed at the time of use, the composition containing as a demixing agent, an effective amount of non-cationic copolymers of vinylpyrrolidone.

2. A composition of claim 1 in which the demixing agent is polyvinylpyrrolidone hexedecene copolymer.

3. The composition of claim 2 in which the oil phase comprises a volatile oil and a non-volatile oil.

4. The composition of claim 1 in which the demixing agent is present in an amount of from about 0.001 to about 10 percent by weight of the total composition 5. The composition of claim 4 in which the volatile oil comprises a volatile silicone and a volatile paraffin.

6. The composition of claim 5 in which the non-volatile oil comprises a non-volatile silicone.

7. The composition of claim 6 which comprises a cyclic silicone present in an amount of about 25 to about 40 percent by weight of the total composition, a $C_{16}$ isoparaffin present in an amount of about 15 to about 30 percent by weight of the total composition, and a non-volatile silicone present in an amount of about 0.1 to about 1 percent by weight of the total composition.

8. The composition of claim 7 in which the cyclic silicone is cyclomethicone, the isoparaffin is isohexadecane, and the non-volatile silicone is dimethicone.

9. The composition of claim 8 which further comprises a surfactant in an amount of no greater than about 5 percent by weight of the total composition.

10. The composition of claim 9 in which the surfactant is present in an amount of about 0.1 to about 1 percent by weight of the total composition.

11. The composition of claim 1 in which the oil phase and the aqueous phase are present in a ratio of about 40:60 to about 60:40.

12. The composition of claim 3 in which the volatile oil is a volatile hydrocarbon.

13. The composition of claim 12 in which the volatile oil is isododecane, isohexadecane or a combination thereof.

\* \* \* \* \*